(12) United States Patent
Tesic et al.

(10) Patent No.: US 8,714,818 B2
(45) Date of Patent: May 6, 2014

(54) REAL-TIME X-RAY MONITORING

(75) Inventors: Mike M. Tesic, Superior, CO (US); James Gessert, Loveland, CO (US)

(73) Assignee: Consensys Imaging Service, Inc., Cary, IL (US)

( * ) Notice: Subject to any disclaimer, the term of this patent is extended or adjusted under 35 U.S.C. 154(b) by 352 days.

(21) Appl. No.: 13/112,829

(22) Filed: May 20, 2011
(Under 37 CFR 1.47)

(65) Prior Publication Data
US 2012/0294419 A1 Nov. 22, 2012

(51) Int. Cl.
*G01D 18/00* (2006.01)
*H05G 1/42* (2006.01)
*H05G 1/44* (2006.01)

(52) U.S. Cl.
USPC .............................. 378/207; 378/97; 378/108

(58) Field of Classification Search
USPC ........... 378/4–20, 95–97, 108, 162, 165, 204, 378/207, 210, 901; 250/354.1, 358.1, 250/359.1, 360.1, 370.01, 370.06, 370.07, 250/370.08, 370.09, 370.11, 371, 394, 395, 250/206, 206.1, 227.29, 227.31
See application file for complete search history.

(56) References Cited

U.S. PATENT DOCUMENTS

| 6,816,564 | B2 * | 11/2004 | Charles et al. ..................... 378/5 |
| 7,573,035 | B2 * | 8/2009 | Levene et al. ............. 250/361 R |
| 2008/0128631 | A1 * | 6/2008 | Suhami ..................... 250/370.09 |
| 2008/0137805 | A1 * | 6/2008 | Forster et al. ................... 378/10 |
| 2009/0067581 | A1 * | 3/2009 | Markoff et al. ............... 378/207 |

* cited by examiner

*Primary Examiner* — Anastasia Midkiff
(74) *Attorney, Agent, or Firm* — Kory D. Christensen; Stoel Rives LLP

(57) ABSTRACT

A medical imaging system has a radiation source, a radiation sensor, a data-collection unit, and an imaging system. The radiation source has an opening to direct a collimated radiation beam in a direction towards a patient. The radiation sensor is disposed proximate the opening and within the collimated radiation beam to measure a fluence of the collimated radiation beam. The data-collection unit is disposed to collect radiation from the collimated beam after interaction with the patient. The imaging system is in communication with the data-collection unit and configured to generate an image of a portion of the patient from the collected radiation.

32 Claims, 6 Drawing Sheets

REAL-TIME X-RAY MONITORING

BACKGROUND OF THE INVENTION

This application relates to diagnostic radiation systems such as x-ray systems. More specifically, this application relates to methods and apparatus for monitoring the operation of diagnostic radiation systems.

Ever since Wilhelm Rontgen discovered x rays and successfully imaged his wife's hand to show the structure of her bones, radiation has been used as a medical diagnostic tool. While two-dimensional radiographs were used for decades, such images suffered from the superposition of images of structures outside the specific region of interest and were generally produced images that were limited to particular image planes.

More recent advances have resulted in the development of tomographic techniques, particularly as embodied in computed-tomography ("CT") imaging devices and in computed axial tomography ("CAT") imaging devices. Since their introduction in the 1970's, tomographic imaging devices have become widely used for both diagnostic and preventive medical applications. In addition to perform CT and CAT scans to confirm suspected diagnoses of tumors, infarction, bone trauma, and the like, scanning using such devices is now almost routine for patients at high risk for certain medical conditions such as colon cancer and heart disease. Indeed, some institutions offer full-body scans to the general public as part of a generalized effort for early detection of disease.

While such efforts have had a significant impact in allowing physicians to detect disease early and to confirm diagnoses without invasive techniques, they are not without a number of concerns. One particular concern results from the fact that x rays are a form of ionizing radiation that have their own impact on the body being measured. Since the early 1980's, the per capita dose of radiation from medical imaging has increased by a factor of almost six. Some estimates suggest that the current level of usage of CT scans will result in an increase in cancer mortality rate of 1.5% to 2% from cancers caused by the scans. While the benefit of reducing cancer mortality from early detection of cancers significantly exceeds this rate, it remains a concern.

Monitoring the actual dose delivered to patient is complicated by a number of factors. The dose depends on multiple known factors that include the volume and type of tissue scanned, the build of the patient scanned, the number and type of scan sequences, and the quality of images to be produced. There is, moreover, a lack of uniformity among machines used to perform the scans, varying not only among manufacturers but also being sufficiently complex devices to have individual variations in uniformity. The dose received by a patient depends on how the machines are used and how different settings for a particular imaging session are configured.

In addition to these patient concerns, there are concerns about the machines themselves. The x-ray tube, for example, tends to degrade over time as the machine is used. To obtain a similar image quality, a machine tends to need to be operated at higher current (mA) as the efficiency of the tube decreases. It is desirable to be able to predict when tube operational quality is likely to become so low that replacement is needed.

There are, thus, a number of deficiencies in the art that it is desirable to address.

SUMMARY

Embodiments of the invention provide a medical imaging system that has a radiation source, a radiation sensor, a data-collection unit, and an imaging system. The radiation source has an opening to direct a collimated radiation beam in a direction towards a patient. The radiation sensor is disposed proximate the opening and within the collimated radiation beam to measure a fluence of the collimated radiation beam. The data-collection unit is disposed to collect radiation from the collimated beam after interaction with the patient. The imaging system is in communication with the data-collection unit and configured to generate an image of a portion of the patient from the collected radiation.

The radiation sensor may comprise a scintillating fiber that emits light in response to absorption of a photon of radiation by the scintillating fiber. A photodetector is coupled with the scintillating fiber to detect emission of light by the scintillating fiber. In some instances, the scintillating fiber may comprise a plurality of scintillating fibers arranged substantially parallel to each other and the photodetector may comprise a plurality of photodetectors with each of the plurality of photodetectors being coupled with one of the plurality of scintillating fibers.

In some embodiments, the radiation sensor has two such arrangements in different orientations. Specifically, the radiation sensor comprises a first radiation sensor and a second radiation sensor. The first radiation sensor has a plurality of scintillating fibers arranged substantially parallel to each other and to a first direction, with each of the first plurality of scintillating fibers emitting light in response to absorption of a photon. Each of a first plurality of photodetectors is coupled with one of the first plurality of scintillating fibers to detect emission of light by the one of the first plurality of scintillating fibers. The second radiation sensor has a second plurality of scintillating fibers arranged substantially parallel to each other and to a second direction, with each of the second plurality of scintillating fibers also emitting light in response to absorption of a photon. Each of a second plurality of photodetectors is coupled with one of the second plurality of scintillating fibers to detect emission of light by the one of the second plurality of scintillating fibers. The first and second directions are nonparallel. In a particular embodiment, the first and second directions may be substantially orthogonal.

The medical imaging system may additionally comprise a monitoring system in communication with the radiation sensor. The monitoring system has instructions to determine an estimate of an effective radiation dose delivered to the patient during an imaging procedure with the medical imaging system from the measured fluence. The radiation sensor may measure a spatial distribution of the fluence and/or it may measure a spectral distribution of the fluence. The medical imaging system may also additionally comprise a mechanism to effect relative translational and/or rotational motion between the radiation source and the patient.

To determine the estimate of the effective radiation dose delivered to the patient, a number of quantities may be obtained: a peak voltage applied to the radiation source to generate the collimated radiation beam, a measure of a geometry of the medical imaging system, a measure of a size of the patient, and a measure of relative motion of the patient with respect to the medical imaging system. In one embodiment, the medical imaging system further comprises a host system in communication with the imaging system and with the radiation source, with each of these quantities being obtained from the host system.

In other embodiments, each of the quantities is instead obtained from an appropriate sensor also comprised by the medical imaging system. For example, the peak voltage applied to the radiation source may be obtained from the measured fluence of the collimated radiation beam. This may include, for example, using spectral information such as the half-value-layer-aluminum. The medical imaging system may further comprise a geometry sensor, with the measure of the geometry of the medical imaging system being obtained from the geometry sensor; examples of suitable geometry sensors include an ultrasound sensor, a laser micrometer, and a visual camera. The medical imaging system may further comprise a patient-size sensor, with the measure of the patient size being obtained from the patient-size sensor; examples of patient-size sensors also include an ultrasound sensor, a laser micrometer, and a visual camera. The medical imaging system may further comprise a motion sensor, with the measure of relative motion of the patient with respect to the medical imaging system being obtained from the motion sensor; the motion sensor might comprise a mechanical sensor, an electromagnetic sensor, or an acoustic sensor. The medical imaging system may further comprise a motion sensor for determining gantry rotation.

The monitoring system may form part of a wider, centrally organized system. Specifically, the monitoring system may be in further communication with a central system that is in communication with a second monitoring system remote from the monitoring system. In such instances, the monitoring system may have instructions to record the estimate of the effective radiation dose delivered to the patient during the imaging procedure at a data store coupled with the central system.

The monitoring system may also may have functionality in addition to determine dose estimates. For example, the monitoring system may identify the measured fluence of the collimated radiation beam as being outside an acceptable range, initiating an alarm in response to such an identification. In other instances, the monitoring system may perform a comparison of the measured fluence of the collimated radiation beam with a record of prior measurements of fluence produced by the radiation source and thereby estimate a time to failure of the radiation source from the comparison.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended to refer collectively to all reference labels that have the same primary label but different sublabels.

DETAILED DESCRIPTION OF EXEMPLARY EMBODIMENTS

Embodiments of the invention are directed generally to methods and apparatus for monitoring the operation of diagnostic radiation systems. While much of the discussion herein focuses on CT imaging devices, it is to be understood that this is by way of illustration only. More generally, the principles applied with the invention may be implemented in a variety of different types of diagnostic systems that use ionizing sources of radiation.

Figure 1:
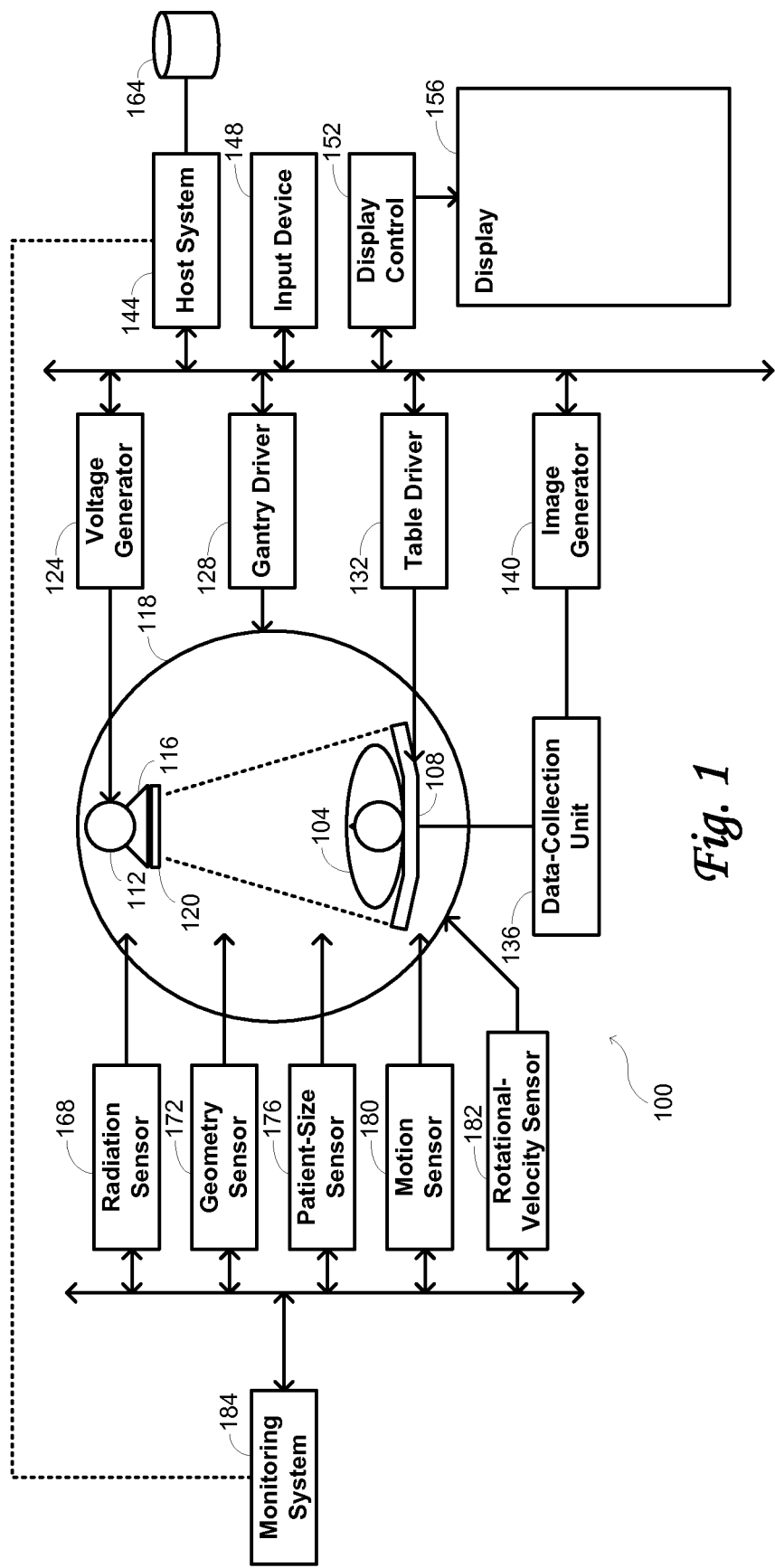
FIG. 1 provides a schematic overview of a CT scanning system as may be used in embodiments of the invention.

One example of a CT system adapted in accordance with embodiments of the invention is illustrated in FIG. 1. In this drawing, the imaging system 100 is shown generally in the middle of the drawing and is adapted for irradiation of a patient 104 in a variety of different modes. Radiation is supplied by a radiation source 112, which may be an x-ray tube of the type well-known in the art. Radiation emitted by the source 112 is collimated by a collimator 116 to direct it towards the patient 104. A filter 120 may optionally be included for spatially varying attenuation of the generated radiation beam. For example, because the human body is generally thicker in the middle and narrower around the edges, a "bowtie" filter may be used to attenuate the radiation beam at its edges while allowing stronger fluence to propagate near the center of the beam.

There may be multiple degrees of freedom of motion, both rotational and translational. Typically, for example the patient 104 is positioned on a table 108 that may move translationally while the beam is subject to rotational motion with a gantry 118 to which the radiation source 112 is coupled. This particular separation of rotational and translational motion is not a constraint of the invention, which may be implemented equally well in systems that may be deployed with other mechanisms for achieved the desired motion. When the table 108 is moved but the gantry 118 is stationary, the beam effectively moves translationally through the patient 104, enabling a series of image slices to be derived. When the gantry 118 is in motion but the table 108 is stationary, the beam moves rotationally, enabling multiple orientation images of structures to be derived to produce an effective three-dimensional image. These can be combined when both the table 108 and gantry 118 are in motion, producing an effective helical beam used in imaging the patient. Generally, both types of motion are at constant rates, although the invention is not limited to such uses and may be adapted to specialized applications as might be developed for varying rates of translational and/or rotational motion.

The various components of the structure are controlled with modules that include a voltage generator 124, a gantry driver 128, a table driver 132, and an image generator 140 that is interfaced with a data collection unit 136. The voltage generator 124 provides tube voltage and current to the radiation source 112 according to instructions received from a host system 144 described in greater detail below. The tube current and voltage are provided in accordance with a mode of operation of the CT system and may vary for different applications. Specific values of the tube current and voltage define the fluence intensity emitted by the radiation source 112. Typical values are 50-150 kV and 100-500 mA, but embodiments of the invention may also use values outside of these ranges.

The gantry driver 128 effects rotational motional of the gantry 118 and may be configured to implement a number of different modalities. For example, the gantry driver 128 may be configured to rotate the gantry a defined forwards or backwards angle so that images may be derived with the radiation source 112 in a specific position relative to the patient 104. Alternatively, the gantry driver 128 may be configured to rotate the gantry 118 continuously for a period of time at a predetermined rate. Typical rates may be around 0.1-2.0 seconds/rotation, but embodiments of the invention may also use values outside of this range.

The table driver 132 similarly effects translational motion of the table 108. The principal translational motions effected by the table driver 132 are in a longitudinal direction, i.e. orthogonal to the page in the drawing, and may provide both discrete motions and continuous motions. Specifically, discrete motions may be used so that the patient 104 is positioned relative to the radiation source 112 for imaging of a defined portion of the body. Continuous motions may be used for imaging of a greater portion of the body by taking slice images as noted above. In addition, it is possible for the table driver 132 to be configured to effect other translational motions of the table 108. For instance, the table driver 132 may be configured to raise or lower the table 108, enabling the patient to be positioned at a desired distance from the radiation source 112. This may be particularly useful in accommodating patients of different sizes so that preferred imaging geometries may be achieved. In addition, the table driver 132 might also be configured for transfer motion of the table 108 to further refine the desired imaging geometry.

The data collection unit 136 may take different positions in different embodiments, depending particularly on acceptable scattering angles for the detected radiation being used for image generation. One position for the data collection unit 136 is beneath the table 108. The data collection unit 136 may take a variety of forms, one example of which comprises an array of radiation-detector elements matched to the spread of a beam irradiated from the radiation source 112.

The image generator 140 is provided in communication with the data collection unit 136 to apply processing methodologies to the collected data in generating an image. Such methodologies may include such known techniques as volume rendering, multiplanar reconstruction, minimum-intensity projection, computed-volume radiography, and the like. For three-dimensional images generated by the image generator 140, relevant supplementary information is generally associated. This may include, for example, information identifying the patient 104. It may also include information defining a visual point of a three-dimensional image obtained from the relevant data and a line of sight determined from the visual point, as well as information of an image-taking direction corresponding to the line of sight, etc.

These various modules are provided in communication with a control system, shown in the drawing as comprising a host system 144, an input device 148, and a display control 152. The host system 144 has access to a storage device 164, which may form part of the control system or which may be separately accessible by the host system 144. One function of the host system 144 is to control the various modules used in defining the imaging geometry, i.e. the gantry driver 128 and the table driver 132, the voltage generator 124 to define the operational characteristics of the imaging procedure, and the image generator 140 itself in defining the type and quality of images to be generated from the procedure.

The host system 144 effects such control by running software that may additionally obtain input parameters from an operator in accordance with the type of imaging to be performed so that the generated images are diagnostically relevant. Such parameters may be provided through the input device 148, which may take a number of different forms in different embodiments. For example, the input device 148 may comprise a touch panel that displays input content with figures or characters selected by the operator, or might comprise a keyboard or other type of interface that allows the receipt of setting values, instructions, and the like from the operator. The display control 152 interacts with the image generator 140 to cause a display of the images produced by the image generator 140 to be shown on a display 156.

The information stored on the data store 164 may vary among different embodiments. In some instances, the data store 164 is used exclusively for the storage of information related to configuring the CT system for an imaging procedure, including software that is run by the host system 144 and a record of parameters used to define certain imaging procedures. Such information includes voltage and current specifications for the radiation source 112, geometry specifications that include whether there is to be relative motion between the radiation source 112 and the patient 104, the type of image to be generated and the like.

In addition to the various components described above, embodiments of the invention additionally include one or more sensors identified generally on the left of the drawing. Such sensors enable an independent determination parameters relevant to determining the radiation dose administered to the patient 104 during an imaging procedure. While there may be instances in which such parameters can be obtained from the control system directly, the deployment of additional sensors as described here enables such parameters to be determined without being supplied by the control system.

A radiation sensor 168 is provided at the output of the collimator 116 and is configured to measure the fluence of the generated radiation beam. In some instances, the fluence may be measured in a single dimension, particularly along the longitudinal direction in which the patient may be moved by the table driver 132. Alternatively, the fluence may be measured in multiple dimensions, particularly along the longitudinal direction but also along the transverse direction, i.e. orthogonal to the longitudinal direction and parallel to the plane of the table 108. Fluence measurements are generally taken concurrently with operation of the system, thereby providing a real-time measurement result of the radiation intensity exiting the collimator 116. If a bowtie or other type of filter is incorporated as discussed above, the radiation sensor 168 may be provided at the output of such a filter.

This information may be combined with information derived from other sensors, which are included with some but not all embodiments of the invention. For instance, a geometry sensor 172 may be used to measure the physical separation of different components of the system, particularly in relation to a position of the patient 104. A patient-size sensor 176 may similarly be deployed to determine physical measurements of the patient 104 and a motion sensor 180 may be used to determine rates of rotational or translational motion of the different components of the system. A rotational-velocity sensor 182 may determine rates of rotational motion of the gantry 118. Each of these additional sensors may thus provide further information relevant in determining the actual radiation dose administered to the patient when combined with information from the radiation sensor regarding the fluence of the radiation beam.

Operation of the various sensors 166, 172, 176, 180, and 182 may be coordinated with a monitoring system 184. The dashed line in the drawing indicates that in some embodiments the monitoring system may be provided in communication with the host system 144, using a wired or wireless connection. When such communication is provided, the monitoring system 184 may exchange information with the control system, such as by using the database 164 coupled with the host system to store relevant information and/or by obtaining information about the parameter settings for an imaging procedure. In cases where such information is available, the monitoring system 184 may use information derived from the sensors as a form of verification and calibration of dose relationships. As will be apparent from the discussion below, the sensor information is capable of providing more accurate dose determinations than the parameter information used by the host system 144 in configuring the CT system.

Figure 2:
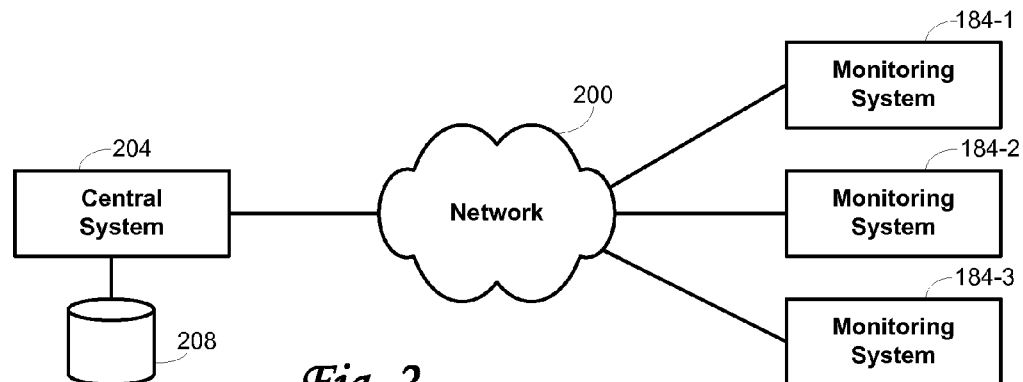
FIG. 2 illustrates a system in which the CT scanning system illustrated in FIG. 1 may be integrated.

The monitoring system 184 may be one of a plurality of monitoring systems that are used to monitor different CT systems. This is illustrated in FIG. 2, which shows a plurality of monitoring systems 184 in communication with a central system 204 through a network 200. The network 200 may comprise a public network such as the Internet in some embodiments, or may comprise a private network. Because some of the information may be sensitive, particularly when patient information is included, it is preferable to use an encryption or other type of security system for communications between the monitoring systems 184 and the central system 204 at least when the network 200 comprises a public network.

With the networked arrangement illustrated in FIG. 2, a database 208 coupled with the central system 204 may be used to integrate information obtained from different monitoring systems 184. Such integration may be particularly useful when monitoring systems 184 are being used to collect information from CT systems produced by the same manufacturer, enabling statistical methods to be applied to the collected data in improving dose, lifetime, and other determinations as described below. In addition, when dose information is associated with particular patient information, the centralized nature of the database 208 permits lifetime patient information to be monitored, even when the patient may have imaging procedures performed at different locations or facilities. Such a capability allows more accurate information to be provided to patients and physicians about lifetime exposure to medical-imaging radiation that may accordingly be a factor in evaluating the risks of future procedures.

Figure 3:
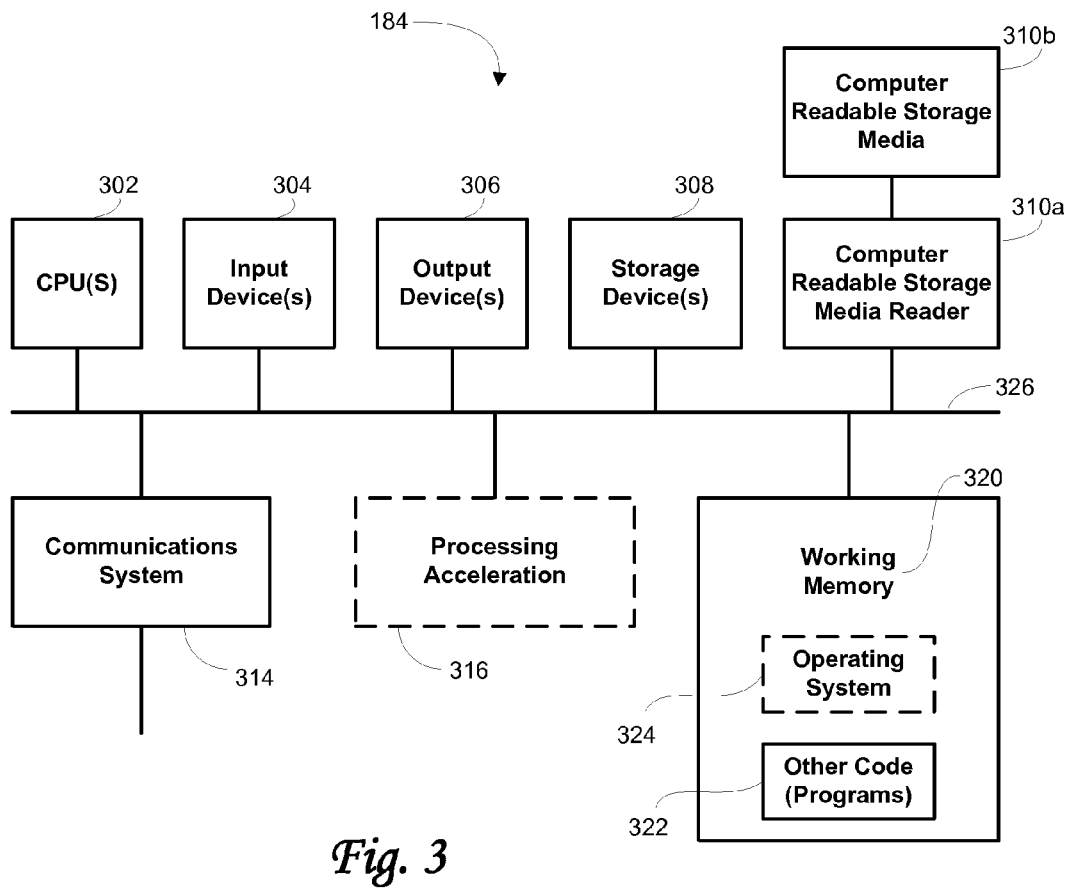
FIG. 3 is a schematic illustration of a structure that may be used for a monitoring system used as part of the CT scanning system of FIG. 1.

A structure that may be used for each of the monitoring systems 184 is shown schematically in FIG. 3. This drawing broadly illustrates how individual system elements may be implemented in a separated or more integrated manner. The monitoring system 184 is shown comprised of hardware elements that are electrically coupled via bus 326. The hardware elements include a processor 302, an input device 304, an output device 306, a storage device 308, a computer-readable storage media reader 310*a*, a communications system 314, and a processing acceleration unit 316 such as a digital-signal processor or special-purpose processor. The computer-readable storage media reader 310*a* is further connected to a computer-readable storage medium 310*b*, the combination comprehensively representing remote, local, fixed, and/or removable storage devices plus storage media for temporarily and/or more permanently containing computer-readable information. The communications system 314 may comprise a wired, wireless, modem, and/or other type of interfacing connection and permits data to be exchanged with external devices.

The monitoring system 184 also comprises software elements, shown as being currently located within working memory 320, including an operating system 324 and other code 322 that may be loaded into working memory on bootup or loaded separately. Such other code may comprise computer programs designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 4:
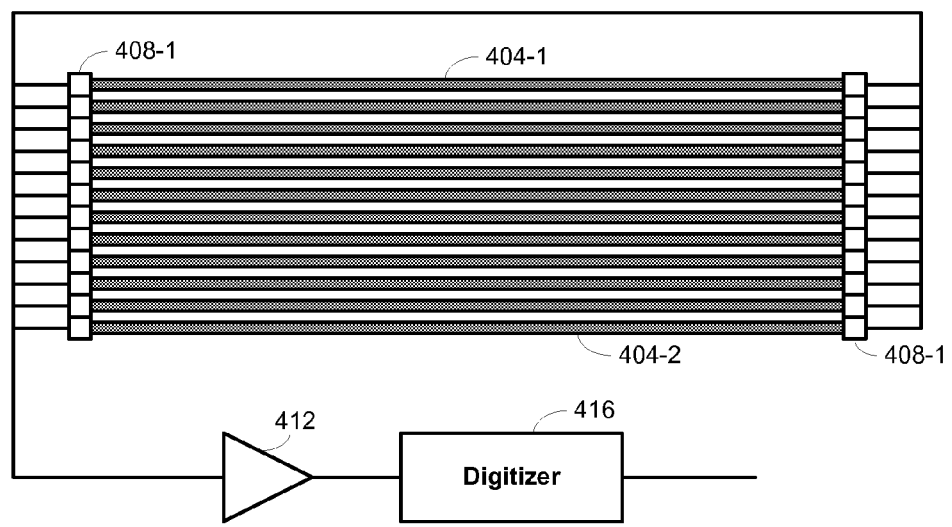
FIG. 4 shows a structure that may be used for an x-ray sensor used with the CT scanning system of FIG. 1.

A structure that may be used for the radiation sensor 168 is illustrated in FIG. 4. This structure comprises a plurality of scintillating fibers 404 coupled at each end with a photosensor 408. Each scintillating fiber comprises a tube that includes a core of scintillating material, possibly including additional dopants to promote scintillation. The scintillating fiber may be made of plastic, and can be homogeneous or made from a plurality of different plastics by having an inner core and a cladding sheath. Scintillating material responds to absorption of radiation by emitting radiation, usually less energetic than what is absorbed. This emitted radiation is detected by the photosensors 408 at the ends of the scintillating fibers, enabling detection of the incident fluence from the radiation source 112. The light intensity detected by the photosensors 408 is a function of the energy and number of photons absorbed, with the number of absorbed photons itself being proportional to the incident fluence and the length of the fiber 404 exposed to the radiation. The light thus generated is converted into an electrical signal for further processing by the photosensors 408. The electrical signal may be amplified with an amplifier 412 and digitized with a digitizer 416 for use by the monitoring system 184.

The use of scintillating fibers advantageously provides a radiation sensor 168 that can be placed directly in the beam path at the collimator output, between the radiation source 112 and the patient 104, because it has very low and relatively uniform x-ray attenuation. This contrasts with conventional detectors that use electronic components, circuit boards, and the like. Such structures are made with copper and other heavy metals that significantly attenuate x rays. By using a scintillating-fiber-based radiation sensor 168, such materials may be disposed elsewhere—outside the x-ray beam. Keeping the electronics out of the x-ray beam also improves the long-term reliability of the radiation sensor 168 because continuous or frequent exposure to high-energy photons can damage and degrade electronic components.

In the illustration, a plurality of fibers 404 are included to provide a measure of the spatial variation of the fluence. By monitoring the electrical signals from all of the fibers concurrently or sequentially, a spatial distribution of the incident radiation beam in the direction orthogonal to the assembly is obtained. In an alternative embodiment, a smaller number of fibers 404 is used and translated across the radiation beam. It is possible to use only a single fiber 404 when such translation is used. A two-dimensional beam distribution may be obtained by using a plurality of the assemblies shown in FIG. 4 oriented at an angle relative to each other. In a particular such embodiment, two assemblies are disposed at approximately 90 degrees relative to each other, enabling the two-dimensional distribution of the fluence from the radiation source to be determined.

By enabling the detection of spatial information about the beam without significant attenuation, the structure of the radiation sensor 168 using scintillating fibers solves an important practical problem. Conventional alternatives of using an ionization chamber, for example, suffer from a lack of providing spatial details. Alternatives of using image-type detectors that provide spatial information have the disadvantage of greatly attenuating the primary beam.

Figure 5:
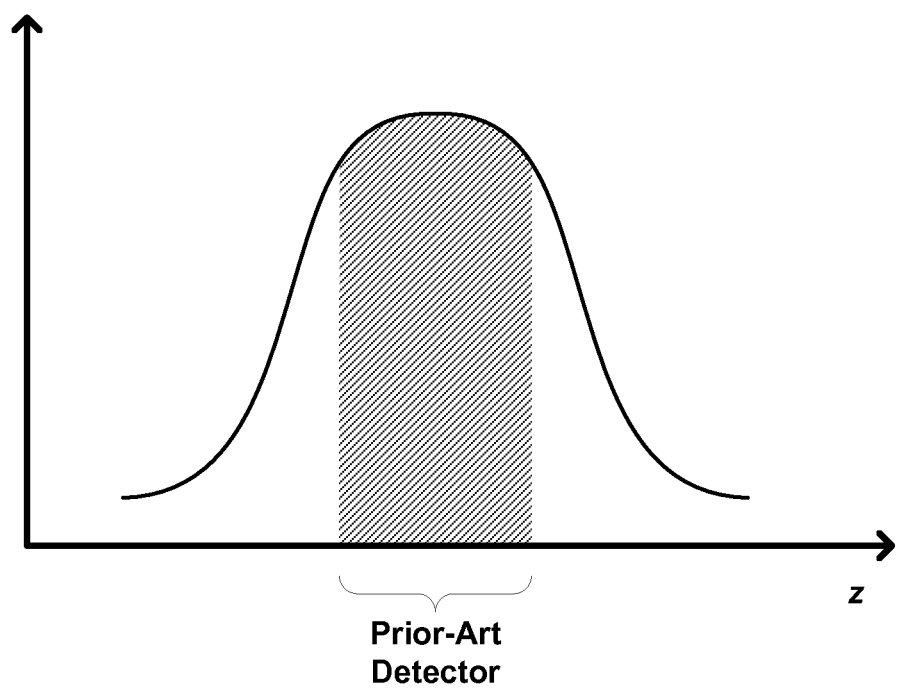
FIG. 5 illustrates measurement of an x-ray beam profile with prior-art detection methods.

FIG. 5 illustrates the raw beam profile generated by the radiation source 112 in the longitudinal direction. Its length in this direction depends on the opening size of the collimator 116, but a prior-art imaging detector is typically narrower than the beam, as illustrated by the shaded portion of the drawing. Such prior-art detectors are thus generally incapable of directly measuring the beam size. The radiation sensor 168 used in embodiments of the invention can be used for this purpose during calibration for measuring beam size for smaller collimator openings than maximum. Even when a patient is being scanned and there can be a large degree of scatter outside the primary beam, the radiation sensor 168 of the invention enables determining that the collimator 116 is correctly positioned.

The fiber structure of the radiation sensor 168 is sufficient to make relative measurements of the beam profile, but it is generally desirable also to be able to determine the photon-energy value to enable a calculation of patient dose and air kerma. This may be achieved with a secondary sensor having a gamma-ray response that is different from that of the scintillating fibers that make up the fiber ribbon. If the secondary sensor is disposed within the primary beam, its attenuation of the beam is preferably low enough not to compromise the ability of the system software to correct for that attenuation.

The geometry sensor 172 may take a variety of different forms in different embodiments, as may the patient-size sensor 176. Each of these sensors may use any form of technology that allows for distance or size measurements. Examples include ultrasound technologies in which acoustic transducers reflect acoustic waves from structures comprised by the system or from different points on the body of the patient and use the echo time to determine the system geometry or the patient size. Other examples include laser micrometers or visual cameras, among a variety of other distance and size technologies known to those of skill in the art.

Similarly, there are a variety of known technologies that may be used to implement motion detection. These include a variety of mechanical, electromagnetic, and acoustic technologies that may be used to provide the motion sensor 180. In one embodiment, accelerometers are used for motion detection.

Figure 6:
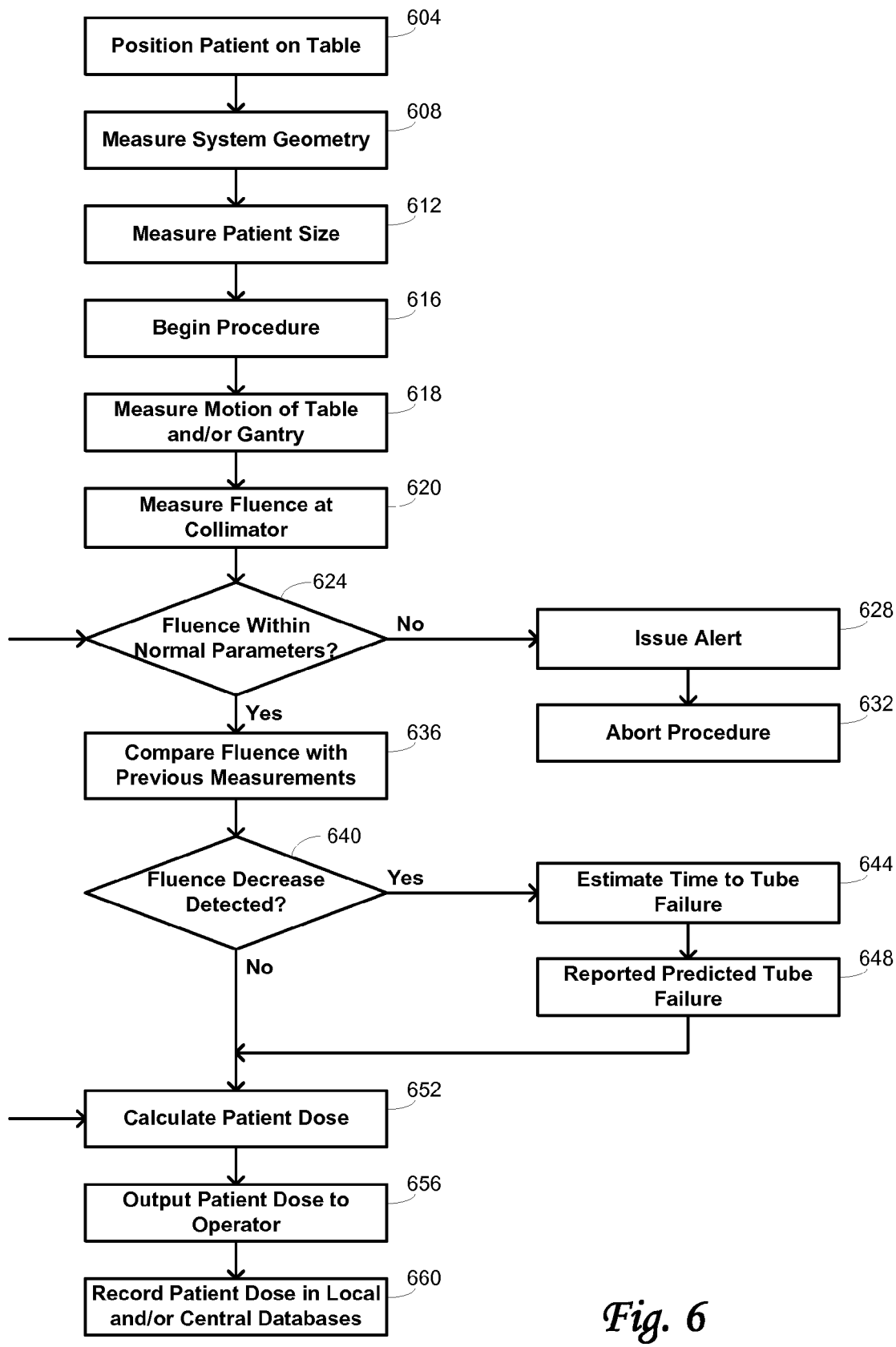
FIG. 6 is a flow diagram summarizing methods of the invention in some embodiments.

Methods of the invention are summarized with the flow diagram of FIG. 6. While the diagram sets forth a number of functions that may be performed in a particular order, this is not intended to be limiting. In alternative embodiments of the invention, some additional functions not specifically identified in the drawing may also be performed, some of the functions specifically called out may be omitted, and/or some of the functions may be performed in an order different from what is set forth. Part of the method includes determination of a radiation dose administered to a patient as part of an imaging procedure and may use the structure described above in connection with FIGS. 1-4.

At block 604, a patient is positioned on the table 108. The patient 104 may take a supine or prone position, or may be placed on her side, depending on the type of imaging to be performed, i.e. whether the data are to be collected to generate a single two-dimensional image, to generate a series of two-dimensional slice images, or to generate a three-dimensional image. As previously noted, these different types of images may be generated using different dynamic configurations of the system. Also relevant in the positioning of the patient 104 is which tissues or structures are to be imaged.

The system geometry is measured with the geometry sensor 172 at block 608 and the patient size is measured at block 612 with the patient-size sensor 176. After the imaging procedure is begun at block 616, any motion of the table 108 and/or gantry 118 may also be measured at block 618, providing a full specification of the dynamical aspects of the procedure performed on the patient. The fluence is measured at block 620 with the radiation sensor 168.

An initial check may be performed on the fluence at block 624 to ensure that the fluence is within normal parameters. The input arrow to this block identifies that information defining standard parameter values may be obtained and used in the evaluation. A deviation from such normal values may prompt the issuance of an alert at block 628 and potential aborting of the procedure at block 632. Such an alert may take the form of an audible and/or visual alert so that a technician overseeing the procedure is notified, and the aborting of the procedure at block 632 may occur automatically or may result from intervention by such a technician. The ability to check the fluence at an exit of the radiation source or collimator permits early intervention, particularly if the fluence is significantly stronger than an acceptable upper limit. This allows accidents that might otherwise result from excessive radiation of a patient to be avoided.

At block 636, a comparison may be made of the measured fluence for the particular procedure with previous measurements. Such comparisons are useful in identifying whether there is a systemic decrease in fluence strength such as may result as the radiation source ages. Such reduction in tube strength is a known consequence of tube aging, requiring the use of higher voltage or current to obtain the desired radiation strength to perform the imaging. If the fluence shows a pattern of decreasing as checked at block 640, it is possible to calculate an estimated time to tube failure at block 644. Such calculations may be performed with a variety of different models of tube behavior that use any number of parameters, including the current and voltage applied to the radiation source 112. Such parameters may also include an identification of the manufacturer of the radiation source 112 since the performance-decay of tubes may differ in a predictable way for tubes provided by different manufactures. The models used in performing such estimates may also make use of past comparisons of fluence levels, which may be collected for multiple systems and recorded by the central system 204 for developing such models.

In addition to performing such comparisons during imaging procedures, the presence of the radiation sensor 168 enables measurements also to be made during calibration procedures. Such calibration procedures are typically performed at regular intervals for each machine, such as by performing a daily calibration. It is noted that this determination of an estimated time to tube failure may be performed without direct information being supplied by the tube manufacturer, allowing an independent check on recommendations for tube replacement that may be made by manufacturers. At block 648, the estimated time to tube failure is accordingly reported, allowing the operator of the machine to integrate a plan for replacement into its normal operating procedures.

At block 652, the patient dose is calculated. The input arrow to this block identifies that parameters used in determining the patient dose may be obtained and used in the calculation. Such calculations may be performed in a number of different ways in different embodiments. Typically, some kind of modeling technique is used rather than a direct calculation because of the complexity of accounting for the different parameters that may impact the actual dose delivered to a patient. In one embodiment, a Monte Carlo model is used to calculate the dose from parameters determined from the measurements collected by the sensors.

Figure 7:
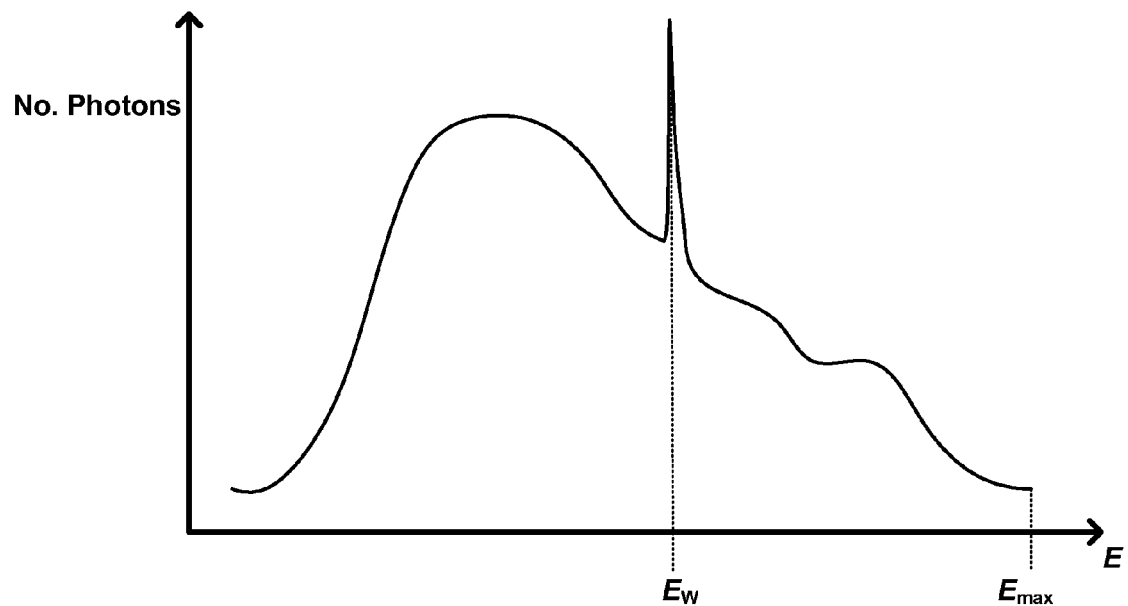
FIG. 7 provides an illustration of a typical spectral distribution of fluence for an x-ray tube.
Figure 8A:
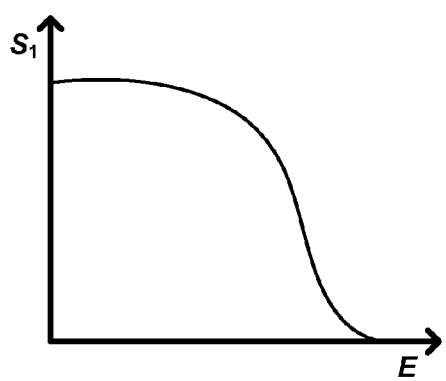
FIG. 8 illustrates different spectral responses of sensors.
Figure 8B:
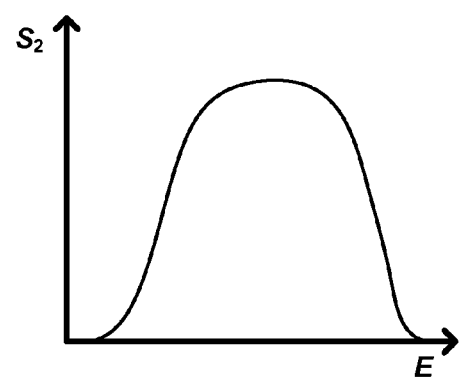

Such parameters include the effective voltage kV and the peak voltage kVp. The peak voltage is the maximum voltage applied across the x-ray tube, defining the kinetic energy of the electrons accelerated within the tube and the corresponding peak energy. FIG. 7 provides an illustration of a spectral distribution of a typical radiation beam that includes a tungsten anode. The distribution has a characteristic peak at the tungsten k-edge energy $E_W$ and terminates at a maximum energy $E_{max}$ that corresponds to the peak voltage kVp, but otherwise has a spectral distribution at different energies. Other types of radiation sources may be used, such as those that use a molybdenum anode and therefore have different characteristic peaks. The peak voltage kVp may be determined by using the secondary sensor having a different gamma-ray response as described above. For example, FIGS. 8A and 8B provide illustrations of different responses that two sensors may have, and the ratio of the responses allows a calculation of the highest energy photons in the beam, as known to those of skill in the art.

In addition to kV and kVp, other parameters that may be determined from sensor measurements and that may accordingly be used in radiation models to permit calculation of the dose include the spatial beam intensity profile, the gantry rotation period, and the patient travel distance, all of which are directly obtained from the radiation sensor 168 and the motion sensor(s). Parameters such as the patient-skin-air kerma with or without tube current modulation may be determined from a combination of patient girth and imaging geometry as may be obtained from measurements by the geometry sensor 172 and the patient-size sensor 176. The physical extent of the dose, i.e. the dose length and the dose volume in helical scans, may be determined from a combination of geometry measurements provided by the geometry sensor 172 and table-motion data as provided by the motion sensor 180.

Models may use these different parameters in combination with a set of tissue absorption characteristics so that the probability of absorbing a photon from the beam may be calculated. This probability is dependent on the photon energy as known from the energy distribution of the beam, on the spatial distribution of the beam, on the size of the patient, on the spatial interaction size between the patient and the beam, and on the patient-skin-air kerma, each of which is determined as described above. It is noted that these values may be determined independently from values calculated by the imaging system itself. Provision of such independent dose information provides increased safety and enhanced evidence-based quality assurance information. Additionally, decoupling the calculation of these safety and performance parameters from the imaging system itself greatly increases the probability that system malfunctions, especially those that could present a patient-safety hazard, are detected.

Returning to FIG. 6, a number of different actions may be taken in response to calculation of the patient dose. For example, as indicated at block 656, the patient dose could be output to an operator of the imaging system as part of providing evaluation information for the procedure. Alternatively or in addition, as indicated at block 660, the patient dose may be recorded in local and/or central databases, such as central database 208, to provide a record of cumulative doses that the patient receives. Such information may aid physicians in evaluating the potential risk of subsequent imaging procedures to be performed on patients.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A medical imaging system comprising:
   a radiation source having an opening to direct a collimated radiation beam in a direction towards a patient;
   a radiation sensor disposed proximate the opening and within the collimated radiation beam to measure a fluence of the collimated radiation beam;
   a data-collection unit disposed to collect radiation from the collimated radiation after interaction with the patient;
   an imaging system in communication with the data-collection unit and configured to generate an image of a portion of the patient from the collected radiation; and
   a monitoring system in communication with the radiation sensor, the monitoring system having instructions to determine an estimate of an effective radiation dose delivered to the patient during an imaging procedure with the medical imaging system from the measured fluence, wherein the instructions comprise:
      instructions to obtain a peak voltage applied to the radiation source to generate the collimated radiation beam;
      instructions to obtain a measure of a geometry of the medical imaging system;
      instructions to obtain a measure of a size of the patient; and
      instructions to obtain a measure of relative motion of the patient with respect to the medical imaging system.

2. The medical imaging system recited in claim 1 wherein the radiation sensor comprises:
   a scintillating fiber that emits light in response to absorption of a photon of radiation by the scintillating fiber; and
   a photodetector coupled with the scintillating fiber to detect emission of light by the scintillating fiber.

3. The medical imaging system recited in claim 2 wherein:
   the scintillating fiber comprises a plurality of scintillating fibers arranged substantially parallel to each other; and
   the photodetector comprises a plurality of photodetectors, each of the plurality of photodetectors being coupled with one of the plurality of scintillating fibers.

4. The medical imaging system recited in claim 1 wherein the radiation sensor comprises:
   a first radiation sensor having:
      a first plurality of scintillating fibers arranged substantially parallel to each other and to a first direction, each of the first plurality of scintillating fibers emitting light in response to absorption of a photon; and
      a first plurality of photodetectors, each of the first plurality of photodetectors coupled with one of the first plurality of scintillating fibers to detect emission of light by the one of the first plurality of scintillating fibers; and
   a second radiation sensor having:
      a second plurality of scintillating fibers arranged substantially parallel to each other and to a second direction, each of the second plurality of scintillating fibers emitting light in response to absorption of a photon; and
      a second plurality of photodetectors, each of the second plurality of photodetectors coupled with one of the second plurality of scintillating fibers to detect emission of light by the one of the second plurality of scintillating fibers,
   wherein the first and second directions are nonparallel.

5. The medical imaging system recited in claim 4 wherein the first and second directions are substantially orthogonal.

6. The medical imaging system recited in claim 1 wherein the radiation sensor measures a spatial distribution of the fluence.

7. The medical imaging system recited in claim 1 wherein the radiation sensor measures a spectral distribution of the fluence.

8. The medical imaging system recited in claim 1 further comprising a mechanism to effect relative translational and/or rotational motion between the radiation source and the patient.

9. The medical imaging system recited in claim 1 further comprising a host system in communication with the imaging system and with the radiation source, wherein:
- the instructions to obtain the peak voltage applied to the radiation source comprise instructions to obtain the peak voltage applied to the radiation source from the host system;
- the instructions to obtain the measure of the geometry of the medical imaging system comprise instructions to obtain the measure of the geometry of the medical imaging system from the host system;
- the instructions to obtain the measure of the size of the patient comprise instructions to obtain the measure of the size of the patient from the host system; and
- the instructions to obtain the measure of relative motion of the patient with respect to the medical imaging system comprise instructions to obtain the measure of relative motion of the patient with respect to the medical imaging system from the host system.

10. The medical imaging system recited in claim 1 wherein the instructions to obtain the peak voltage applied to the radiation source comprise instructions to obtain the peak voltage applied to the radiation source from the measured fluence of the collimated radiation beam.

11. The medical imaging system recited in claim 1 further comprising a geometry sensor, wherein the instructions to obtain the measure of the geometry of the medical imaging system comprise instructions to obtain the measure of the geometry of the medical imaging system from the geometry sensor.

12. The medical imaging system recited in claim 11 wherein the geometry sensor comprises a sensor selected from the group consisting of an ultrasound sensor, a laser micrometer, and a visual camera.

13. The medical imaging system recited in claim 1 further comprising a patient-size sensor, wherein the instructions to obtain the measure of the size of the patient comprise instructions to obtain the measure of the size of the patient from the patient-size sensor.

14. The medical imaging system recited in claim 13 wherein the patient-size sensor comprises a sensor selected from the group consisting of an ultrasound sensor, a laser micrometer, and a visual camera.

15. The medical imaging system recited in claim 1 further comprising a motion sensor, wherein the instructions to obtain the measure of relative motion of the patient with respect to the medical imaging system comprise instructions to obtain the measure of relative motion of the patient with respect to the medical imaging system from the motion sensor.

16. The medical imaging system recited in claim 15 wherein the motion sensor comprises a mechanical sensor, an electromagnetic sensor, or an acoustic sensor.

17. The medical imaging system recited in claim 1 wherein the monitoring system is further in communication with a central system that is in communication with a second monitoring system remote from the monitoring system.

18. The medical imaging system recited in claim 17 wherein the monitoring system further has instructions to record the estimate of the effective radiation dose delivered to the patient during the imaging procedure at a data store coupled with the central system.

19. The medical imaging system recited in claim 1 wherein the monitoring system further has:
- instructions to identify the measured fluence of the collimated radiation beam as being outside an acceptable range; and
- instructions to initiate an alarm in response to identifying the measured fluence being outside the acceptable range.

20. The medical imaging system recited in claim 1 wherein the monitoring the system further has:
- instructions to perform a comparison of the measured fluence of the collimated radiation beam with a record of prior measurements of fluence produced by the radiation source; and
- instructions to estimate a time to failure of the radiation source from the comparison.

21. A method of monitoring a medical imaging system comprising a radiation source having an opening to direct a collimated radiation beam in a direction towards a patient, a mechanism to effect relative translational and/or rotational motion between the radiation source and the patient, and an imaging system configured to generate an image of a portion of the patient from radiation collected from the collimated radiation beam after interaction with the patient, the method comprising:
- measuring a fluence of the collimated radiation beam with a radiation sensor disposed proximate the opening and within the collimated radiation beam; and
- determining an estimate of an effective radiation dose delivered to the patient during an imaging procedure with the medical imaging system from the measured fluence by:
  - obtaining a peak voltage applied to the radiation source to generate the collimated radiation beam;
  - obtaining a measure of a geometry of the medical imaging system;
  - obtaining a measure of a size of the patient; and
  - obtaining a measure of relative motion of the patient with respect to the medical imaging system.

22. The method recited in claim 21 wherein the radiation sensor comprises:
- a scintillating fiber that emits light in response to absorption of a photon of radiation by the scintillating fiber; and
- a photodetector coupled with the scintillating fiber to detect emission of light by the scintillating fiber.

23. The method recited in claim 22 wherein:
- the scintillating fiber comprises a plurality of scintillating fibers arranged substantially parallel to each other; and
- the photodetector comprises a plurality of photodetectors, each of the plurality of photodetectors being coupled with one of the plurality of scintillating fibers.

24. The method recited in claim 21 wherein the radiation sensor comprises:
- a first radiation sensor having:
  - a first plurality of scintillating fibers arranged substantially parallel to each other and to a first direction, each of the first plurality of scintillating fibers emitting light in response to absorption of a photon; and
  - a first plurality of photodetectors, each of the first plurality of photodetectors coupled with one of the first plurality of scintillating fibers to detect emission of light by the one of the first plurality of scintillating fibers; and a second radiation sensor having:
  a second plurality of scintillating fibers arranged substantially parallel to each other and to a second direction, each of the second plurality of scintillating fibers emitting light in response to absorption of a photon; and
  a second plurality of photodetectors, each of the second plurality of photodetectors coupled with one of the second plurality of scintillating fibers to detect emission of light by the one of the second plurality of scintillating fibers,
wherein the first and second directions are nonparallel.

25. The method recited in claim 24 wherein the first and second directions are substantially orthogonal.

26. The method recited in claim 21 wherein measuring the fluence of the collimated radiation beam comprises measuring a spatial distribution of the fluence.

27. The method recited in claim 21 wherein measuring the fluence of the collimated radiation beam comprises measuring a spectral distribution of the fluence.

28. The method recited in claim 21 wherein:
  the medical imaging system further comprises a host system in communication with the imaging system, the radiation source, and the mechanism;
  obtaining the peak voltage applied to the radiation source comprises obtaining the peak voltage applied to the radiation source from the host system;
  obtaining the measure of the geometry of the medical imaging system comprises obtaining the measure of the geometry of the medical imaging system from the host system;
  obtaining the measure of the size of the patient comprises obtaining the measure of the size of the patient from the host system; and
  obtaining the measure of relative motion of the patient with respect to the medical imaging system comprises obtaining the measure of relative motion of the patient with respect to the medical imaging system from the host system.

29. The method recited in claim 21 wherein:
  obtaining the peak voltage applied to the radiation source comprises determining the peak voltage applied to the radiation source from the measured fluence;
  obtaining the measure of the geometry of the medical imaging system comprises measuring the geometry of the medical imaging system with a geometry sensor;
  obtaining the measure of the size of the patient comprises measuring the size of the patient with a patient-size sensor; and
  obtaining the measure of relative motion of the patient with respect to the medical imaging system comprises measuring the relative motion of the patient with respect to the medical imaging system with a motion sensor.

30. The method recited in claim 21 further comprising transmitting the estimate of the effective radiation dose delivered to the patient during the imaging procedure to a central system for storing the estimate.

31. The method recited in claim 21 further comprising:
  identifying the measured fluence of the collimated radiation beam as being outside an acceptable range; and
  initiating an alarm in response to identifying the measured fluence being outside the acceptable range.

32. The method recited in claim 21 further comprising:
  performing a comparison of the measured fluence of the collimated radiation beam with a record of prior measurements of fluence produced by the radiation source; and
  estimating a time to failure of the radiation source from the comparison.

\* \* \* \* \*